United States Patent [19]
Eaton

[11] Patent Number: 6,146,419
[45] Date of Patent: Nov. 14, 2000

[54] METHOD FOR FORMING A HOLLOW PROSTHESIS

[75] Inventor: L. Daniel Eaton, Little Rock, Ark.

[73] Assignee: Board of Trustees of the University, Little Rock, Ark.

[21] Appl. No.: 09/518,358

[22] Filed: Mar. 3, 2000

Related U.S. Application Data

[62] Division of application No. 09/311,431, May 13, 1999.
[51] Int. Cl.$^7$ ........................................... A61F 2/02
[52] U.S. Cl. ........................ 623/11.11; 264/222; 623/901
[58] Field of Search ................................ 623/11.1, 17.11, 623/17.12, 17.16, 901, 7, 8; 264/222

[56] References Cited

U.S. PATENT DOCUMENTS

| | | |
|---|---|---|
| 2,580,264 | 12/1951 | Wright et al. . |
| 3,366,975 | 2/1968 | Pangman . |
| 3,854,507 | 12/1974 | Kirby et al. . |
| 3,860,969 | 1/1975 | Arion . |
| 3,867,728 | 2/1975 | Stubstad et al. . |
| 3,897,376 | 7/1975 | Lampe . |
| 3,905,376 | 9/1975 | Johnson et al. . |
| 3,925,277 | 12/1975 | Lampe . |
| 4,086,666 | 5/1978 | Vaskys et al. . |
| 4,253,201 | 3/1981 | Ross et al. . |
| 4,263,682 | 4/1981 | Bejarano . |
| 4,401,492 | 8/1983 | Pfrommer . |
| 4,531,244 | 7/1985 | Hamas . |
| 4,546,899 | 10/1985 | Williams . |
| 4,549,529 | 10/1985 | White . |
| 4,574,780 | 3/1986 | Manders . |
| 4,643,733 | 2/1987 | Becker . |
| 4,661,187 | 4/1987 | Beasley . |
| 4,668,567 | 5/1987 | Williams . |
| 4,671,255 | 6/1987 | Dubrul et al. . |
| 4,676,795 | 6/1987 | Grundei . |
| 4,731,081 | 3/1988 | Tiffany et al. . |
| 4,735,754 | 4/1988 | Buckner . |
| 4,826,501 | 5/1989 | Grundei . |
| 4,863,477 | 9/1989 | Monson . |
| 4,902,294 | 2/1990 | Gosserez . |
| 4,932,969 | 6/1990 | Frey et al. . |
| 4,944,749 | 7/1990 | Becker . |
| 4,995,882 | 2/1991 | Destouet et al. . |
| 5,005,591 | 4/1991 | Austad . |
| 5,019,101 | 5/1991 | Purkait et al. . |
| 5,035,758 | 7/1991 | Deiger et al. . |
| 5,071,443 | 12/1991 | Bühler et al. . |
| 5,091,121 | 2/1992 | Nakada et al. . |
| 5,098,330 | 3/1992 | Greenburg . |
| 5,108,430 | 4/1992 | Ravo . |
| 5,123,926 | 6/1992 | Pisharodi . |
| 5,133,753 | 7/1992 | Bark et al. . |
| 5,282,856 | 2/1994 | Ledergerber . |
| 5,303,718 | 4/1994 | Krajicek . |
| 5,308,420 | 5/1994 | Yang . |
| 5,314,478 | 5/1994 | Oka et al. . |
| 5,352,307 | 10/1994 | Wild . |
| 5,358,521 | 10/1994 | Shane . |
| 5,376,323 | 12/1994 | Eaton . |
| 5,496,367 | 3/1996 | Fisher . |
| 5,496,370 | 3/1996 | Hamas . |
| 5,514,180 | 5/1996 | Heggeness et al. . |
| 5,527,359 | 6/1996 | Nakamura et al. . |
| 5,545,229 | 8/1996 | Parsons et al. . |
| 5,549,679 | 8/1996 | Kuslich . |
| 5,554,180 | 9/1996 | Turk . |
| 5,607,473 | 3/1997 | Weber-Unger et al. . |
| 5,632,777 | 5/1997 | Petrick . |
| 5,645,597 | 7/1997 | Krapiva . |
| 5,658,329 | 8/1997 | Purkait . |
| 5,658,330 | 8/1997 | Carlisle et al. . |
| 5,693,099 | 12/1997 | Harle . |
| 5,700,288 | 12/1997 | Eaton . |
| 5,702,446 | 12/1997 | Schenck et al. . |
| 5,702,454 | 12/1997 | Baumgartner . |
| 5,824,093 | 10/1998 | Ray et al. . |
| 5,855,606 | 1/1999 | Eaton . |

FOREIGN PATENT DOCUMENTS

| | | |
|---|---|---|
| 392960 | 10/1990 | European Pat. Off. . |
| 4115428 | 11/1992 | Germany . |
| 2202745 | 10/1988 | United Kingdom . |

*Primary Examiner*—Jeffrey A. Smith
*Assistant Examiner*—Eduardo C. Robert
*Attorney, Agent, or Firm*—Ray F. Cox, Jr.

[57] ABSTRACT

An alloplastic device and process for replacement of a damaged or diseased spinal vertebral column disk. The replacement disk is hollow room temperature vulcanizable (RTV) silicone shaped to mimic the natural disk being replaced. The shape can be derived from a mold of the natural disk or an MRI scan. The replacement disk may be trabeculated (honeycombed) and may be filled with a lubricating fluid including triglyceride oil, preferably soybean oil. The replacement disk is formed by allowing RTV silicone injected into a mold to vulcanize at room temperatures until a wall of sufficient thickness is formed. The unvulcanized silicone is expressed to form the hollow interior. The replacement disk is formed with a nipple having an interior concavity. The nipple is cut from the body of the replacement disk leaving an opening into the hollow interior. The nipple is inverted and sealed into the opening so that the nipple extends from the surface of the replacement disk into the interior where it contacts the opposite wall of the disk. The inverted nipple thus provides a central support for the disk and a valve structure to inject the lubricating fluid into the hollow interior. The concavity of the inverted nipple is filled with RTV silicone which then vulcanizes and seals the opening. The hollow disk lubricates itself since the lubricating fluid percolates slowly through the silicone wall. Other uses include replacement for a worn out or injured miniscus, and other orthopedic applications including carpal tunnel damage or injuries.

7 Claims, 3 Drawing Sheets

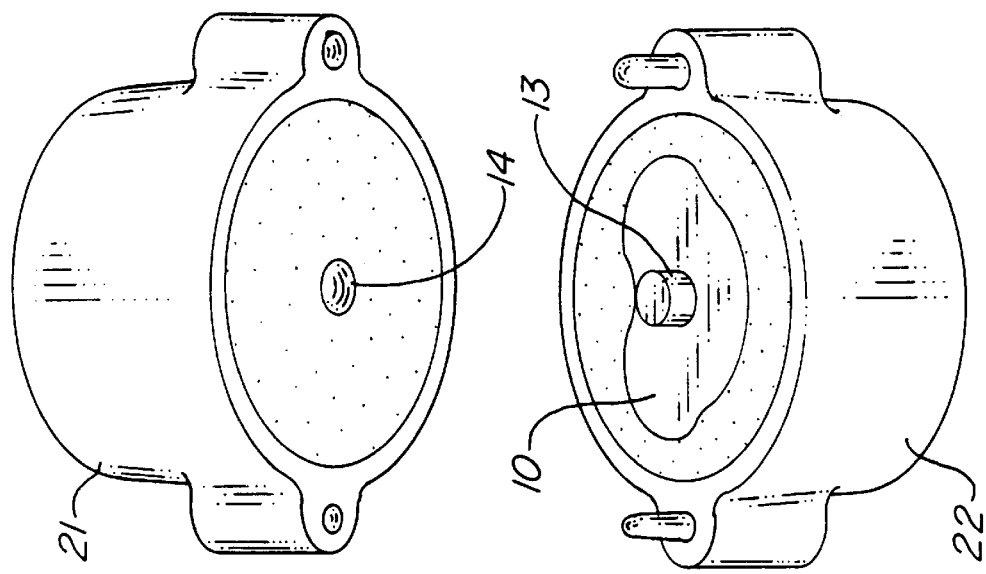
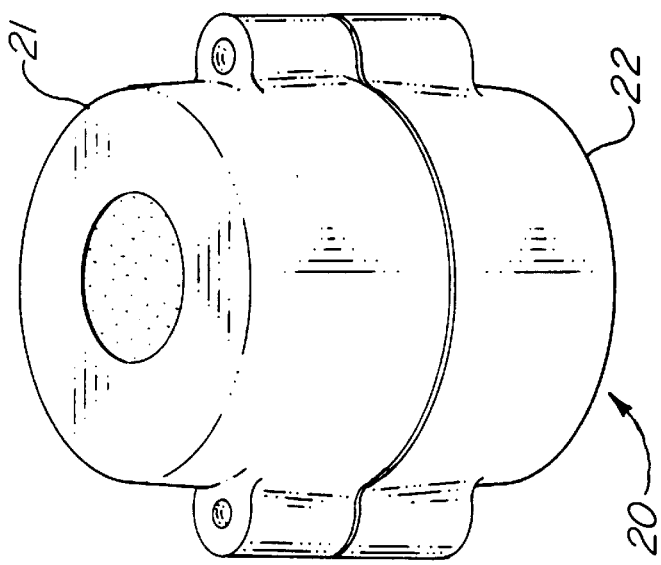

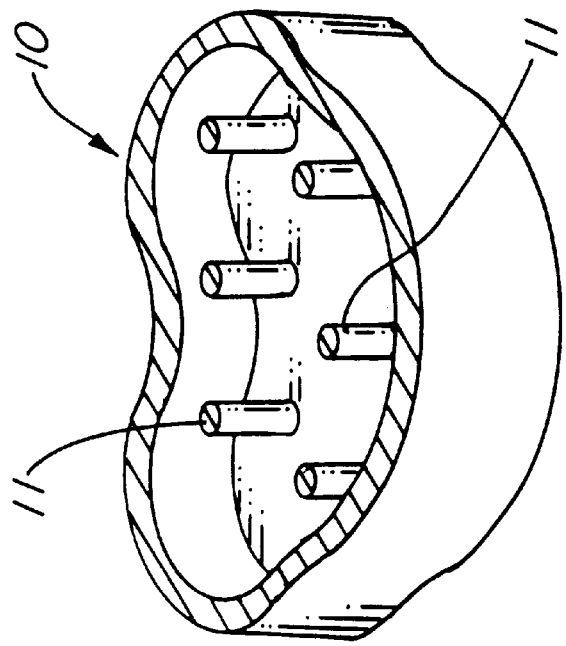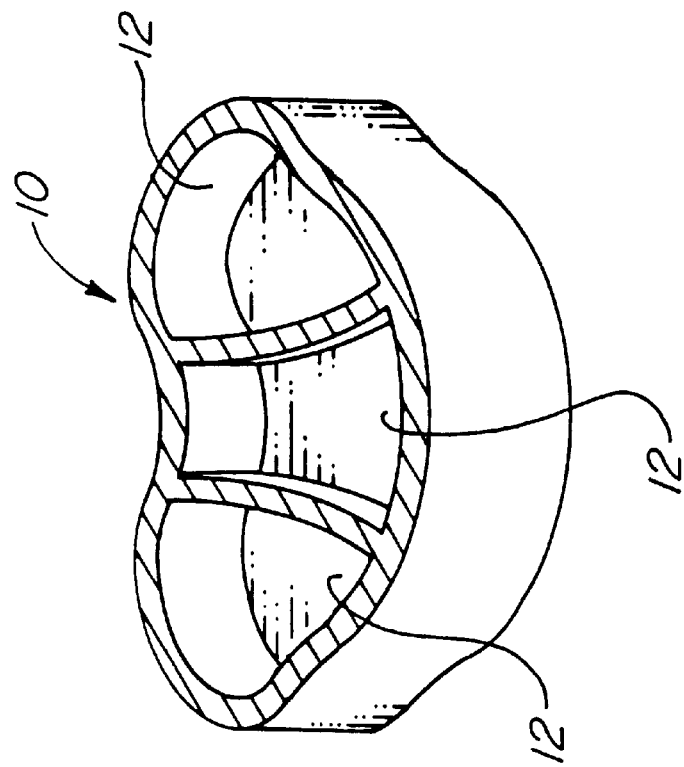

METHOD FOR FORMING A HOLLOW PROSTHESIS

This application is a divisional of copending application Ser. No. 09/311,431 filed on May 13, 1999.

BACKGROUND OF THE INVENTION

The present invention relates to devices for the replacement of interverterbral disks damaged or destroyed by disease or trauma, and in particular, to a hollow prosthetic device and a method of forming a hollow prosthetic device having a fluid infusion port which is sealed to prevent leakage.

When intervertebral disks are damaged or destroyed by disease or trauma, total removal of the disk is often indicated. Reconstruction or replacement of the function performed by the lost disk may require the use of autografts or allografts to fuse the adjacent vertebrae together. A more complete and natural restoration of function is possible with the implantation of prosthetic intervertebral disks.

U.S. Pat. No. 5,514,180 discloses intervertebral prosthetic devices having fixed shapes for accommodating the defined surface contours of the vertebral endplates. The invention defines five morphological types of surfaces comprising a set of surfaces capable of accommodating the anatomy of most vertebral endplates. A method of digitizing the surface of a vertebral body to determine a specific shape of a vertebral endplate is also disclosed. Furthermore this invention also relates to such prosthetic devices incorporating osteoinductive material such as bone growth factors.

U.S. Patent No. discloses a method for replacing the nucleus pulposus of an intervertebral disk. The nucleus pulposus is removed and a flexible hollow prosthetic disk is inserted into the space defined by the annulus fibrosis. The prosthetic disk is then filled with a gel material.

U.S. Pat. No. 5,545,229 discloses an intervertebral disk spacer comprising a central core of soft elastomer approximating the size and shape of the nucleus pulposus, an outer ring of stiffer elastomeric material approximating the size and shape of the annulus fibrosis, and endplates of stiff material incorporating a mechanism for attachment to the adjacent bony vertebral bodies.

U.S. Pat. No. 4,863,477 discloses an intervertebral disk prosthesis molded in the shape of the natural disk. The replacement disk is molded of rubber or silicone rubber. The replacement disk is formed from two halves joined together to form a hollow interior. After the disk is implanted between two vertebrae, a fluid, such as saline, is injected into the hollow interior space.

Various techniques are know for forming hollow prostheses. A technique developed by the inventor of the present invention is disclosed in U.S. Pat. Nos. 5,376,323; 5,855,606 and 5,700,288. The technique disclosed in these patents utilizes room temperature vulcanizable silicone. Room temperature vulcanizable silicone compositions are described generally in U.S. Pat. Nos. 3,925,277 and 3,897,376. A technique for forming prosthetic devices having varying degrees of flexibility is disclosed in U.S. Pat. No. 4,735,754 to Buckner. This technique selectively removes silicone material from the device to form voids having the requisite degree of flexibility.

U.S. Pat. No. 5,314,478 discloses a prosthesis that may be used as a replacement for an intervertebral disk. The prosthesis is a composite of polyvinyl alcohol hydrogel and a ceramic or metallic porous body.

U.S. Pat. No. 5,824,093 discloses a prosthetic spinal disk comprising a jacket surrounding a hydrogel core that is allowed to hydrate to a predetermined volume.

U.S. Pat. No. 5,702,454 discloses a prosthetic implant for replacing a spinal disk. Support members are inserted into a cavity in the core of the intervertebral disk until the cavity is filled.

U.S. Pat. No. 3,867,728 discloses a prosthesis for spinal repair comprising a core element having a flat top and bottom surfaces. The core is made of elastic polymer and may be reinforced. A covering element secured to both flat surfaces provides a tissue ingrowth receptive material.

The limitations of the prior art are overcome by the present invention as described below.

SUMMARY OF THE INVENTION

The present invention is an alloplastic device for replacement of a damaged, ruptured, disintegrated or diseased spinal vertebral column disk and a method of forming such a replacement disk. The replacement disk is hollow elastomer, preferably room temperature vulcanizable (RTV) silicone, such as Silastic® medical adhesive silicone Type A (available from Dow Corning). The replacement disk is shaped to mimic the natural disk being replaced. The shape can be derived from a mold of the natural disk, if intact, or from a composite of fragments of the natural disk. If the natural disk is too fragmented or altered by disease or trauma or otherwise does not present a good model for the development of a mold of the replacement device, an MRI scan can be used to develop the shape of the mold using known techniques such as computerized numerically controlled shaping machines.

The hollow elastomeric shape may be produced by the technique disclosed in U.S. Pat. No. 5,376,323, which is incorporated herein by reference. This technique allows various wall thicknesses to be formed depending on the load bearing requirements of the replacement disk. In addition, the replacement disk may be trabeculated or honeycombed with multiple chambers or multiple load bearing pillars. The hollow disk may be filled with a triglyceride oil, such as soybean oil or rice oil, cerebrospinal fluid, seroma or synovial fluid, or a combination of any of these materials.

In the preferred embodiment the replacement disk is formed by allowing room temperature vulcanizable (RTV) silicone, such as Silastic®, injected into a mold to vulcanize at room temperatures until a wall of sufficient thickness is formed. The unvulcanized RTV silicone is expressed to form the hollow interior. The replacement disk is formed with a nipple having an interior concavity. Once the replacement disk is removed from the mold and the unvulcanized RTV silicone expressed from the interior, the nipple is cut from the body of the replacement disk leaving an opening into the hollow interior. The nipple is inverted and sealed into the opening so that the nipple extends from the surface of the replacement disk down into the interior where it contacts the opposite wall of the disk. The inverted nipple thus provides a central support for the disk. More importantly, the inverted nipple provides an infusion port to inject a lubricating fluid, such as soybean oil, into the hollow interior of the disk. It should be understood that vulcanized RTV silicone is not self-sealing. Using the inverted nipple infusion port, however, the lubricating fluid is injected by a hypodermic needle into the sidewall of the infusion port. After the proper amount of fluid is injected, the concavity of the infusion port is filled with RTV silicone, which then vulcanizes and seals the opening.

The disk is surgically positioned between two spinal vertebra to separate and provide a cushion against movement and compaction in the manner of a natural disk. The replacement disk also provides shock absorption and maintains an appropriate and accurate distance between the vertebrae for safety, comfort and motility of the spinal column.

The hollow disk also lubricates itself since a triglyceride oil filing material, such as soybean oil in the preferred embodiment, percolates slowly through the silicone wall. A mixture of soybean oil and synovial fluid continually lubricates the surfaces in the space between the vertebrae and the replacement disk. Genetic engineering of the structural formulas of soybean oil, seroma, and synovial fluid could be employed to optimize the molecular size of the fluids for the lubrication function.

The present invention provides definitive intervention for chronic physical problems, including pain. It is a solution for the problem of the ruptured disk and provides an alternative to vertebral fusion. The present invention may also allow correction of problems due to trauma. Although described primarily as a vertebral disk replacement, the present invention is not so limited. Other uses include replacement for a worn out or injured miniscus, and other orthopedic applications including carpal tunnel damage or injuries.

It is therefore an object of the present invention to provide for a hollow prosthesis formed with a nipple having an interior concavity for inversion and use as an infusion port to inject the filling material.

It is a further object of the present invention to provide for a filling material comprising a triglyceride oil, such as soybean oil or rice oil, for a hollow prosthesis in combination with a permeable wall for the hollow prosthesis in order to allow the prosthesis to be self-lubricating.

These and other objects and advantages of the present invention will be apparent from a consideration of the following detailed description of the preferred embodiments in conjunction with the appended drawings as described following.

BRIEF DESCRIPTION OF THE DRAWINGS

FIG. 1 is a perspective view of a mold for a replacement vertebral disk.

FIG. 2 is an exploded perspective view of the mold of FIG. 1 showing the shapes of the upper and lower halves of the mold and a molded prosthesis in the lower half. The prosthesis is shown with a nipple molded into the prosthesis and the indentation in the upper half of the mold for producing the nipple.

FIG. 4A shows the cross section of the prosthesis as it appears from the mold. FIG. 4B shows the nipple removed from the prosthesis, inverted and affixed into the interior of the prosthesis to form the infusion port. FIG. 4C shows the prosthesis being filled with a filling material by hypodermic needle injected into the sidewall of the infusion port.

FIG. 4D shows the interior concavity of the infusion port sealed to prevent leakage of the filling material.

FIG. 5 shows a perspective view of a sectioned prosthesis. In this embodiment the interior of the prosthesis is honeycombed; i.e., divided into a plurality of chambers.

FIG. 6 shows a perspective view of a sectioned prosthesis. In this embodiment the interior is trabeculated; i.e., provided with a plurality of load bearing pillars.

DETAILED DESCRIPTION OF THE PREFERRED EMBODIMENTS

The present invention is an alloplastic device for replacement of a damaged, ruptured, disintegrated or diseased spinal vertebral column disk and a method of forming such a replacement disk. The replacement disk is a hollow prosthesis formed from an elastomer, preferably a room temperature vulcanizable (RTV) silicone, such as Silastic® medical adhesive silicone Type A (available from Dow Corning).

Figure 3:
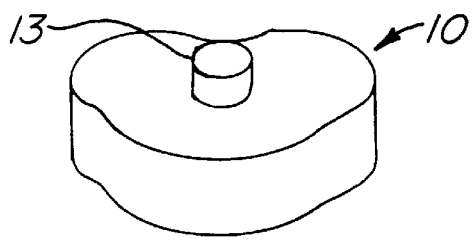
FIG. 3 is a perspective view of the prosthesis removed from the mold of FIG. 2

With reference to FIGS. 1–3, the replacement disk 10 is shaped to mimic the natural disk being replaced. The shape can be derived from a mold of the natural disk, if intact, or from a composite of fragments of the natural disk. If the natural disk is too fragmented or altered by disease or trauma or otherwise does not present a good model for the development of a mold of the replacement device, an MRI scan can be used to develop an image of the space occupied by the natural disk using known techniques such as computerized numerically controlled shaping machines. From the shape thus determined, a mold can be produced.

The mold 20 for producing the replacement disk 10 can be a two piece mold having an upper portion 21 and a lower portion 22. The hollow elastomeric shape of the replacement disk 10 may be produced by the technique disclosed in U.S. Pat. No. 5,376,323, which is incorporated herein by reference. This technique allows various wall thicknesses to be formed depending on the load bearing requirements of the replacement disk 10. For example, cervical disks may not require walls as thick as would be appropriate for lumbar or sacral disks. If allowed to completely vulcanize, a solid disk may be formed for maximum load bearing capability. In addition, the replacement disk 10 may be trabeculated with multiple load bearing posts 11 as shown in FIG. 6 or honeycombed with multiple chambers 12 as shown in FIG. 5. In the later embodiments, the technique disclosed in U.S. Pat. No. 5,376,323 may not be appropriate and more complicated molding procedures may be required.

As may be seen from FIGS. 2 and 3, the lower portion 22 of the mold 20 replicates the shape desired in the replacement disk 10 by replicating the shape of a natural disk. An additional feature not found in the natural disk is a nipple 13 formed on the replacement disk 10 by sculpting an indentation 14 in the upper portion 21 of the mold 20. The significance of the nipple 13 is discussed more fully below.

Figure 4A:
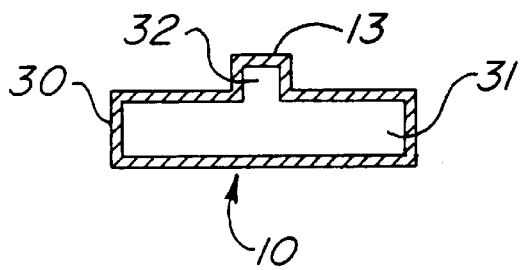
FIGS. 4A–4D are sequence of elevational cross-sections of the prosthesis of FIG. 3.
Figure 4C:
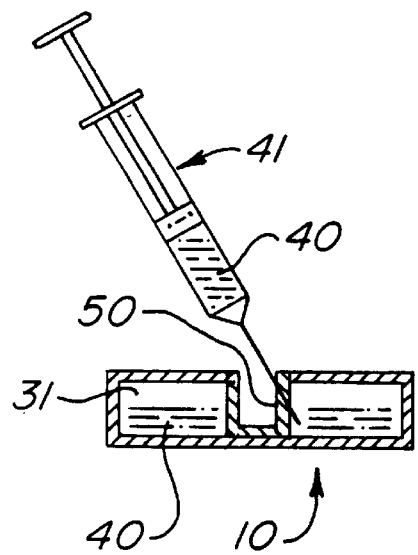

In the preferred embodiment the replacement disk 10 is formed by allowing room temperature vulcanizable (RTV) silicone, such as Silastic® medical adhesive silicone Type A, injected into the mold 20 to vulcanize at room temperatures until a wall 30 of sufficient thickness is formed as shown in FIG. 4A. The thickness of the wall 30 is determined by the load bearing requirements of the replacement disk 10. The unvulcanized RTV silicone within the replacement disk 10 is expressed to form the hollow interior 31. The replacement disk 10 is thus formed with the nipple 13 having an interior concavity 32.

Figure 4B:
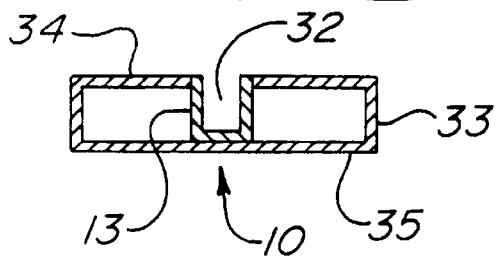
Figure 4D:
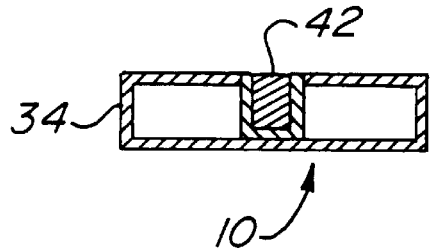

Once the replacement disk 10 is removed from the mold 20 and the unvulcanized RTV silicone expressed from the interior 31, the nipple 13 is cut from the body 33 of the replacement disk leaving an opening in the upper surface 34 of the replacement disk 10 into the hollow interior 31. As shown in FIG. 4B, the nipple 13 is inverted and sealed into the opening on the upper surface 34 so that the nipple 13 extends from the upper surface 34 of the replacement disk 10 down into the interior 31 where it contacts the lower surface 35 of the disk 10. The inverted nipple may be sealed to the lower surface 35 using silicone or the like. The inverted nipple 13 thus provides a central support for the disk 10. In other embodiments of the present invention the inverted nipple 13 need not actually contact or be bonded to the lower surface 35. If the disk 10 is to be formed as a solid disk, the nipple 13 may be removed and discarded.

The main function of the inverted nipple 13 is to provide an infusion port to inject a lubricating fluid, such as soybean oil or other triglyceride oil, or other filling material 40 into the hollow interior 31 of the disk. It should be understood that vulcanized RTV silicone is not self-sealing. Using the inverted nipple 13 as an infusion port, however, the filling material 40 is injected by a hypodermic needle 41 into a sidewall 50 of the inverted nipple 13. After the proper amount of filling material 40 is injected, the concavity 32 of the inverted nipple 13 is filled with RTV silicone which then vulcanizes and forms a plug 42 which seals the opening. It is thus possible to manufacture a seamless hollow prosthesis and to fill the hollow prosthesis even though the prosthesis is constructed of material that is not self-sealing.

The filling material 40 in the preferred embodiment is a triglyceride oil, such as soybean oil or rice oil. The filling material 40 may also be cerebrospinal fluid, seroma, synovial fluid, or a combination of these lubricating fluids. The preferred filling material 40 is soybean oil (trilipid Z5), which is a natural triglyceride and has been used for 40 years as an I.M. drug carrier. There is thus a long history of the safe application of soybean oil to human patients.

It has been determined that the hollow replacement disk 10 lubricates itself since soybean oil percolates slowly through the semi-permeable silicone wall 30. In the preferred embodiment, a mixture of soybean oil and synovial fluid continually lubricates the surfaces in the space between the vertebrae and the replacement disk 10. Genetic engineering of the structural formula of soybean oil, seroma, and synovial fluid could be employed to optimize the molecular size of the fluids for the lubrication function.

An experimental prototype of RTV silicone was vulcanized, filled with soybean oil and a soybean oil/seroma combination. The prototype was demonstrated to hold a vacuum and that the infusion port did not leak. The prototype also demonstrated percolation of the soybean oil and soybean oil/seroma combination through the semipermeable wall of the prototype.

After the replacement disk 10 has been manufactured and the appropriate filling material injected into the replacement disk 10, the disk 10 is surgically positioned between two spinal vertebrae to separate and provide a cushion against movement and compaction in the manner of a natural disk. The replacement disk 10 also provides shock absorption and maintains an appropriate and accurate distance between the vertebrae for safety, comfort and motility of the spinal column.

Although the present invention has been described with reference to an embodiment in which the prosthesis is a replacement for a vertebral disk, the invention is not so limited and would be applicable other prosthetic devices where self-lubrication is desirable. Other uses include, without limitation, replacement for a worn out or injured miniscus, and other orthopedic applications including carpal tunnel damage or injuries.

The present invention has been described with reference to certain preferred and alternative embodiments that are intended to be exemplary only and not limiting to the full scope of the present invention as set forth in the appended claims.

What is claimed is:

1. A method of forming a hollow prosthesis, comprising the steps of:
   (a) forming a mold having the shape of the desired prosthesis, said mold further having a depression for forming a nipple on the surface of the prosthesis;
   (b) injecting said mold with room temperature vulcanizable silicone;
   (c) allowing sufficient time for walls of vulcanized silicone to form on the interior surfaces of the mold to a desired thickness so that the nipple retains an interior concavity;
   (d) removing the prosthesis from the mold and expressing unvulcanized silicone from the interior of the prosthesis; and
   (e) excising the nipple from the prosthesis, inverting the nipple into the opening thus created into the hollow interior of the prosthesis, and sealing the nipple into the wall of the prosthesis.

2. The method of claim 1 further comprising the steps of injecting filling material into the interior of the prosthesis through the concavity of the inverted nipple and sealing the concavity with room temperature vulcanizable silicone.

3. The method of claim 2 wherein said filling material comprises a triglyceride oil.

4. The method of claim 3 wherein said triglyceride oil comprises soybean oil.

5. The method of claim 4 wherein said prosthesis is molded into the shape of an intervertebral disk.

6. The method of claim 5 wherein step (a) comprises taking an impression of a natural intervertebral disk and forming the mold from the impression of the natural intervertebral disk.

7. The method of claim 5 wherein step (a) comprises scanning an intervertebral disk space, forming an impression of the intervertebral disk space by computerized numerically controlled shaping, and forming the mold from the impression.

\* \* \* \* \*